(12) United States Patent
Landgrebe

(10) Patent No.: US 6,638,209 B2
(45) Date of Patent: Oct. 28, 2003

(54) SYSTEM WITH A SURGICAL NEEDLE AND A HANDLE

(75) Inventor: Susanne Landgrebe, Sulfeld (DE)

(73) Assignee: Ethicon GmbH, Norderstedt (DE)

(*) Notice: Subject to any disclaimer, the term of this patent is extended or adjusted under 35 U.S.C. 154(b) by 0 days.

(21) Appl. No.: 09/956,363

(22) Filed: Sep. 19, 2001

(65) Prior Publication Data

US 2002/0091298 A1 Jul. 11, 2002

Related U.S. Application Data

(60) Provisional application No. 60/242,271, filed on Oct. 20, 2000.

(51) Int. Cl.$^7$ .................................................. A61F 2/02
(52) U.S. Cl. ........................... 600/30; 600/29; 606/119; 606/148
(58) Field of Search ................................ 606/119, 139, 606/140, 147, 148, 222; 600/29, 30, 135, 564, 565, 566, 567

(56) References Cited

U.S. PATENT DOCUMENTS

| | | | | |
|---|---|---|---|---|
| 4,172,458 A | * | 10/1979 | Pereyra | 600/567 |
| 4,256,119 A | * | 3/1981 | Gauthier | 600/567 |
| 4,487,209 A | * | 12/1984 | Mehl | 600/567 |
| 4,898,589 A | * | 2/1990 | Dolgin et al. | 604/198 |
| 5,019,032 A | * | 5/1991 | Robertson | 403/292 |
| 5,090,419 A | * | 2/1992 | Palestrant | 600/567 |
| 5,323,765 A | | 6/1994 | Brown | |
| 5,331,972 A | * | 7/1994 | Wadhwani et al. | 600/567 |
| 5,474,565 A | | 12/1995 | Trott | |
| 5,807,275 A | * | 9/1998 | Jamshidi | 606/118 |
| 5,843,001 A | * | 12/1998 | Goldenberg | 128/DIG. 25 |
| 5,899,909 A | | 5/1999 | Claren et al. | |
| 6,030,393 A | * | 2/2000 | Corlew | 606/144 |
| 6,221,029 B1 | * | 4/2001 | Mathis et al. | 600/564 |
| 6,273,852 B1 | | 8/2001 | Lehe et al. | |
| 6,468,279 B1 | * | 10/2002 | Reo | 606/79 |
| 6,554,778 B1 | * | 4/2003 | Fleming, III | 600/567 |

OTHER PUBLICATIONS

PCT International Search Report, dated Aug. 6, 2002, for PCT Int'l. Appln. No PCT/EP01/11988.

* cited by examiner

Primary Examiner—Max F. Hindenburg
Assistant Examiner—Jonathan Foerman

(57) ABSTRACT

In a system with a surgical needle (10) and a handle (20), the surgical needle (10), in its proximal end region opposite the needle tip, includes a support section which is adapted to be pushed in the handle (20). The handle (20) includes a lumen adapted to support the support section of the surgical needle (10) and a locking device (30, 26), which can be adjusted from a locking position, in which the support section is secured to the handle (20), to a release position, in which the support section can be pulled out of the lumen.

13 Claims, 6 Drawing Sheets

FIG. 11a
FIG. 11b
FIG. 11c
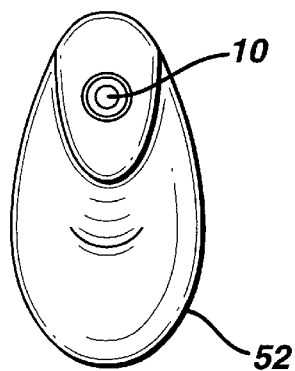
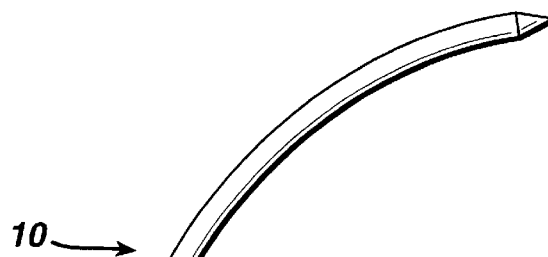
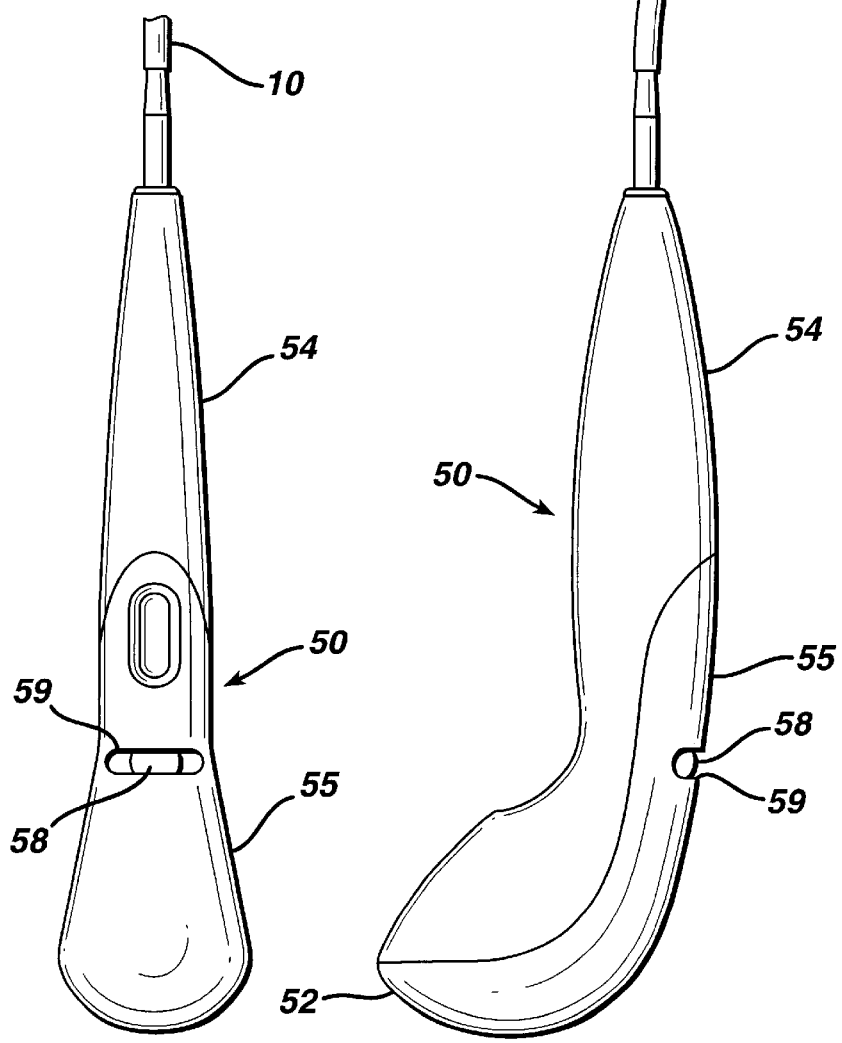

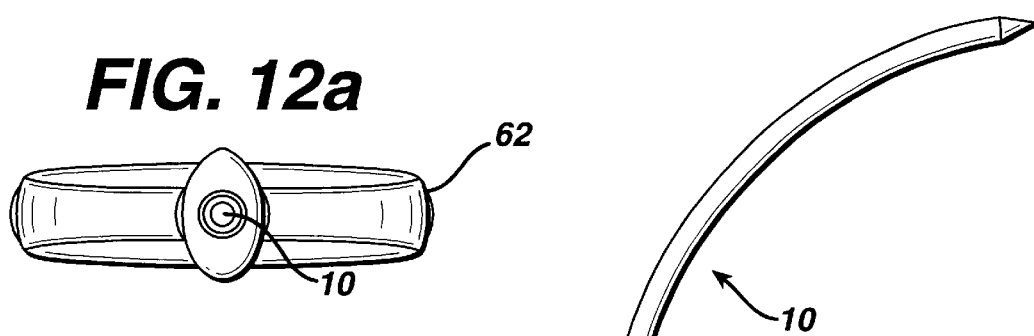
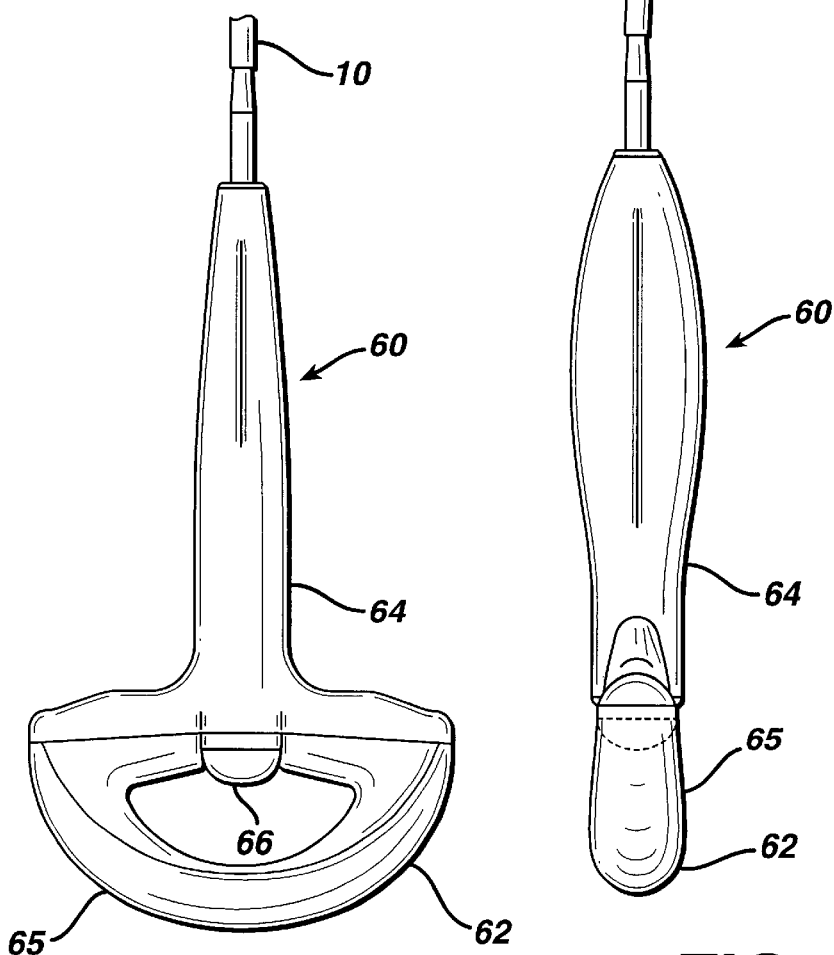
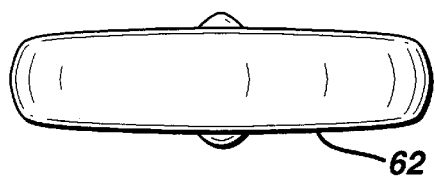

SYSTEM WITH A SURGICAL NEEDLE AND A HANDLE

CROSS REFERENCE TO RELATED APPLICATION

The present invention claims the benefit of earlier-filed U.S. provisional patent application, Ser. No. 60/242,271, filed on Oct. 20, 2000, which is hereby incorporated by reference in its entirety herein.

FIELD OF THE INVENTION

The invention relates to a system with a surgical needle and a handle.

BACKGROUND OF THE INVENTION

There are surgical operation techniques in which thick or very thick surgical needles are used, e.g., needles having a diameter from 2 mm to 7 mm. For example, such needles are used in order to insert a band or tape below the urethra of a patient for treatment of stress incontinence as disclosed in U.S. Pat. Nos. 5,899,909 and U.S. Pat. No. 6,273,852, both incorporated by reference herein in their entirety.

When the needle is guided through tissue, considerable forces occur. In handling the needle, the surgeon can use a needle holder or a gripper-like surgical instrument as an aid, but, as a rule, he has to re-apply this instrument to the needle often, which is not convenient. Moreover, unfavorable lever ratios can occur, in particular if the instrument runs oblique with respect to the needle.

SUMMARY OF THE INVENTION

It is an object of the invention to provide a possibility for facilitating the handling of a surgical needle, in particular of a thick surgical needle.

The system according to the invention includes a surgical needle and a handle. The surgical needle comprises, in its proximal end region opposite the needle tip, a support section, which is adapted for pushing into the handle. The handle comprises a lumen adapted for holding the support section of the surgical needle and a locking means. The locking means can be switched from a locking position, in which the support section is fixed to the handle, to a release position, in which the support section can be pulled out of the lumen.

When the support section is locked or fixed at the handle, the surgical needle is rigidly and securely connected to the handle. In this state, the handle appreciably facilitates the handling of the needle. For example, by means of the handle, the needle can be held and easily guided through the tissue of the patient. The suture material, tape or a similar object, which is to be pulled through the tissue by means of the needle, can be attached to the shaft of the surgical needle in between the support section and the needle tip, preferably close to the support section, by means of a shrink tubing or other attachment and detachment means as is disclosed in U.S. Pat. No. 6,273,852 B1, incorporated by reference herein in its entirety. If shrink tubing is used as the attachment means, the surgical needle preferably comprises an attachment section for suture material, a tape or similar means, distal to the support section, e.g. a corrugated section of the shaft which can also be provided with a step at which the shrink tubing engages in order to enable a continuous transition between the shaft and the suture material, the tape or similar means.

When using the invention for the method disclosed in the U.S. Pat. No. 5,899,909, after the needle has penetrated the abdomen the needle tip can be grasped by the surgeon by hand (or with a conventional instrument). At this moment, the locking means can be switched from the locking position to the release position, such that the needle can be pulled out of the handle non-abruptly and with a small force effort (or, vice versa, the handle can be retracted from the needle). After releasing the handle, the needle with the suture material, tape or similar means attached to the needle can be completely pulled through the tissue.

The surgical needle can have a diameter of 2 mm to 7 mm, but a different diameter is conceivable as well. Certainly, as is known to those skilled in the art, the surgical needle may take on any variety of cross-sections.

Preferably, the support section of the surgical needle, in its cross-section, at least in a partial region deviates from a circular shape, and the lumen, in its cross-section, is adapted to the support section for securing the surgical needle against torsion. This design enables a torsion-proof connection of the needle to the handle in a simple manner.

In an advantageous version of the invention, the lumen starts at an opening in the distal end region of the handle, and the support section of the surgical needle is adapted to a longitudinal insertion into this opening. The support section of the surgical needle comprises a depression, into which, in the locking position, engages a locking element provided at the locking means of the handle. The locking means comprises a sleeve rotatably mounted in the lumen of the handle. In this preferred embodiment, there is provided at the proximal end of the support section of the surgical needle adjacent to the depression of the support section, a locking protrusion having a non-circular cross-sectional shape. The sleeve of the locking means is rotatable around the longitudinal axis of the lumen from the locking position into the release position and comprises a plate-like locking element having an opening which can be passed by the locking protrusion in the release position, but not in the locking position. Preferably, the locking element is located in the distal end region of the sleeve. The sleeve can be coupled to an actuating lever, which essentially runs in radial direction, the free end of the actuating lever preferably extending through an opening in the handle, which opening allows a rotational movement of the actuating lever and sleeve. The handle can include an engagement means for securing the actuating lever in the locking position.

This preferred embodiment of the invention allows a convenient and safe handling of the surgical needle with one hand. If required, the actuating lever can be moved into the release position, e.g., by means of the thumb, such that the surgical needle can be released from the handle with a small force and virtually without a jerk. Thus, the surgeon requires one hand only in order to operate the system. Another advantage of this embodiment is that it can be immediately recognized by means of the position of the actuating lever whether the locking means is in the locking position or the release position.

Preferably, the handle is made from synthetic material and can be designed as a disposable article. Preferably, the handle has a two-part casing such that the locking means can be easily assembled.

In a preferred embodiment of the invention, the handle, in the area of its proximal end, comprises at least one broadening structure, e.g., two protrusions, which extend into opposite directions and transversely with respect to the surgical needle, which protrusions enable the handle to rest conveniently in the surgeon's palm or ball of the thumb. The handle can additionally comprise at least one finger application structure, e.g. two wing-like structures extending into opposite directions, which run in parallel to the broadening structures and by means of which the surgeon, e.g. using the index finger and the middle finger, can pull the handle onto his palm such that it securely rests in his hand. Another advantage of this embodiment becomes apparent when the needle is curved. In this case the surgeon can recognize the direction of the leading (distal) end of the needle area in relation to the position of the broadening structure or the finger application structure.

These and other features and advantages of the present invention will become apparent from the following more detailed description, when taken in conjunction with the accompanying drawings which illustrate, by way of example, the principles of the invention.

BRIEF DESCRIPTION OF THE DRAWINGS

In the following, the invention is explained in more detail by means of embodiments.

FIGS. 11a–d are several views of a third embodiment of the system according to the invention, i.e. (a) an elevation view from the distal end of the handle (b) a plan view of the handle, (c) an elevation view, and (d) a schematic exploded view; and FIGS. 12a–d are several views of a fourth embodiment of the system according to the invention, i.e. (a) an elevation view from the distal end of the handle, (b) a plan view of the handle, (c) an elevation view from the proximal end of the handle, and (d) an elevation view.

DETAILED DESCRIPTION OF THE PREFERRED EMBODIMENT

Before explaining the present invention in detail, it should be noted that the invention is not limited in its application or use to the details of construction and arrangement of parts illustrated in the accompanying drawings and description, because the illustrative embodiments of the invention may be implemented or incorporated in other embodiments, variations and modifications, and may be practiced or carried out in various ways. Furthermore, unless otherwise indicated, the terms and expressions employed herein have been chosen for the purpose of describing the illustrative embodiments of the present invention.

Figure 1:
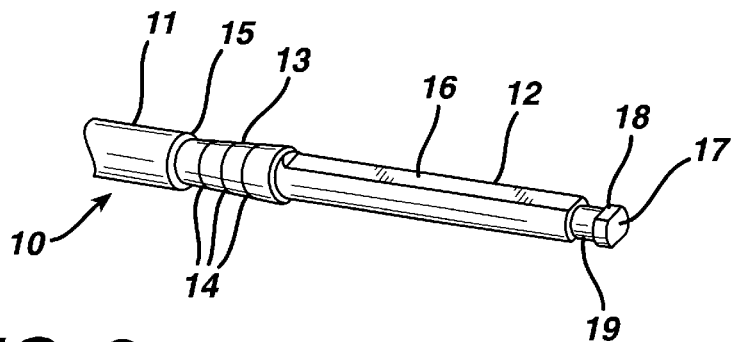
FIG. 1 is a perspective view of the proximal end region of the surgical needle in an embodiment of the system according to the invention.

FIG. 1 illustrates in a perspective view the proximal end region of a surgical needle 10, which is one component of an embodiment of the system with a surgical needle and a handle. The needle tip, which is located at the distal end of the needle 10, is not shown in FIG. 1. A shaft 11, joins to the needle tip. In its proximal end region, the needle 10 comprises a support section 12.

An attachment section 13, which, in the embodiment, has a conical basic shape (the diameter increasing in the proximal direction) and is provided with a corrugation 14, is located between the shaft 11 and the support section 12. At the transition between the shaft 11 and the attachment section 13, there is formed a step or shoulder 15. At the attachment section 13, e. g. a tape can be attached, e.g. by means of shrink tubing, which is to be secured in the tissue of a patient by means of the surgical needle 10. The step 15 provides for a smooth change of the cross-section between the needle 10 and the shrink tubing or the tape at the transition site. Alternative means may be provided to attach the tape at both the proximal end and the distal end of the needle 10.

The support section 12 has a cross-sectional shape with two flat portions, from which one can be seen in FIG. 1 and is designated by 16. A locking protrusion 17, the cross-sectional shape of which coincides to that in the distal region of the support section 12, is located at the proximal end of the support section 12; the cross-sectional shape corresponds to the area 34 in FIG. 7. The locking protrusion 17 has two flat portions as well, from which one is designated by 18 and can be seen in FIG. 1. Adjacent to the locking protrusion 17 in distal direction, there is a depression 19. In the embodiment, the cross-sectional shape of the needle 10 is circular in the area of the depression 19, the diameter corresponding to the distance between both flat portions 18 of the locking protrusion 17.

Preferably, the surgical needle 10 is integrally made and, in the region of the shaft 11 and the needle tip, can have any form suitable to the desired application.

Figure 2:
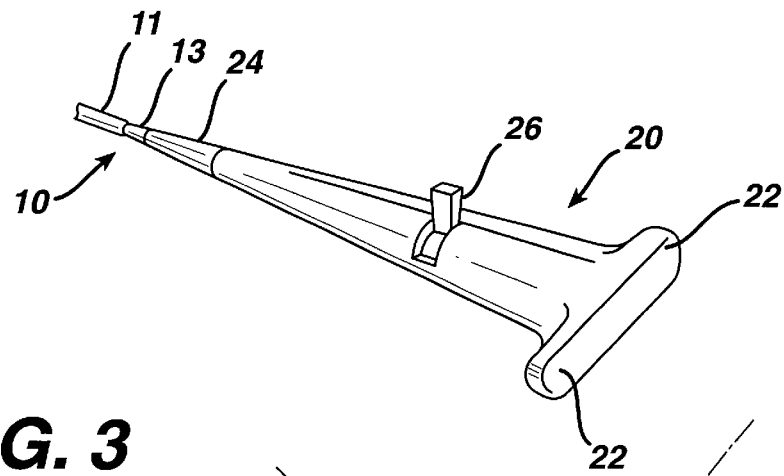
FIG. 2 is a perspective view of the handle in the embodiment of the system according to the invention.
Figure 3:
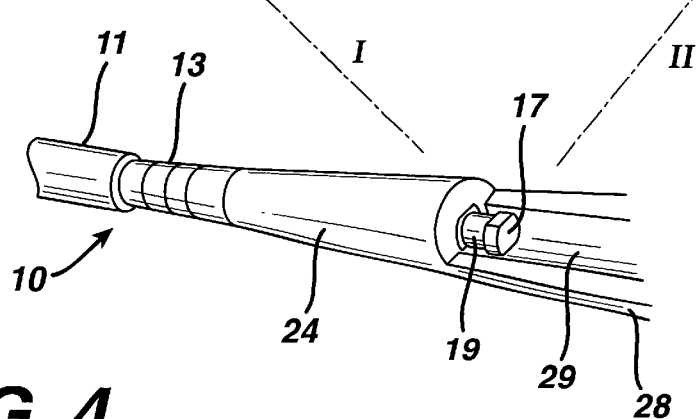
FIG. 3 is a perspective view of the distal region of the handle when the casing is opened and the surgical needle is inserted.

FIGS. 2 and 3 illustrate a handle 20, which is another component of the system. In the area of its proximal end, the handle 20 is provided with two broadening structures 22, which cause the handle to rest well in a surgeon's hand. A duct or lumen, into which the support section 12 of the needle 10 can be pushed, is located in the distal end region 24 of the handle 20, as explained below in detail. In the views according to FIGS. 2 and 3, the needle 10 is inserted in the handle 20 such that only the attachment section 13 and the shaft 11 only of the needle 10 are not inserted into the handle 20. In the middle area of the handle 20, an actuating lever 26 functions as a locking means for easily locking and unlocking the needle 10, as discussed below. In the embodiment, the handle 20 is made from synthetic material and has a casing with a lower casing part 28 and an upper casing part. It is designed as a disposable article. A reusable handle, however, is conceivable as well.

FIG. 3 shows the distal region of the lower casing part 28 with a surgical needle 10 inserted. The lower casing part 28 includes, in its distal end region 24, a lumen running in the longitudinal direction of the handle 20, which lumen is closed in circumferential direction and open at the distal end face of the handle 20 and at the proximal end of the lumen. The cross-sectional shape of this lumen is adapted to that of the support section 12, its length corresponds to that of the flat portion 16. Thus, the support section 12 of the needle 10 can be pushed into the lumen from the distal end face of the handle 20 and thereafter section 12 is supported in the lumen in a torsion-proof manner. As can be seen in FIG. 3, the depression 19 and the locking protrusion 17 are external to the lumen when the needle 10 is inserted into handle 20.

Joining to the lumen in proximal direction, there is formed a channel 29 in the lower casing part 28, as indicated in FIG. 3. The channel 29 is accessible when the casing of the handle 20 is opened. In the assembled state of the handle, a sleeve 30 (see FIG. 4) is mounted between the channel 29 and a similarly designed channel in the upper casing 38 (FIG. 6) such that the sleeve 30 can be rotated around the longitudinal axis of the channel 29 between a locking position and a release position.

Figure 4:
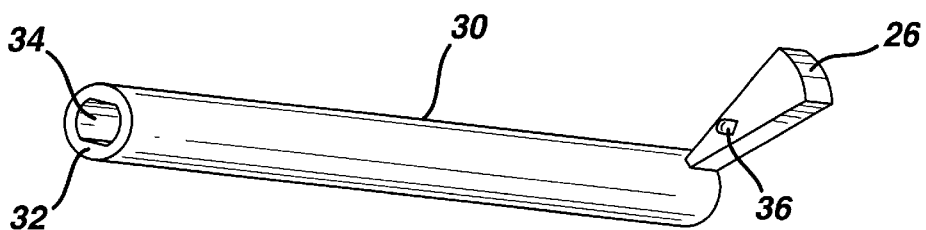
FIG. 4 is a perspective view of the locking means of the handle in the embodiment of the system according to the invention.

As shown in FIG. 4, the sleeve 30 has a circular cross-section. At its distal end face, the sleeve 30 is designed as a plate-like locking element 32, which is provided with an opening 34. The opening 34 (see also FIG. 7) is adapted with respect to the shape of the cross-sectional shape of the locking protrusion 17 such that the locking protrusion 17 can pass through the opening 34 if the flat portions 18 and the corresponding flat portions of the opening 34 are aligned with respect to each other. In the assembled state of the handle 20, the distal end of sleeve 30 abuts at the proximal end of the lumen for the support section 12 such that the depression 19 is located in the area of the locking element 32; the thickness of the locking element 32 is adapted to the length of the depression 19.

Figure 5:
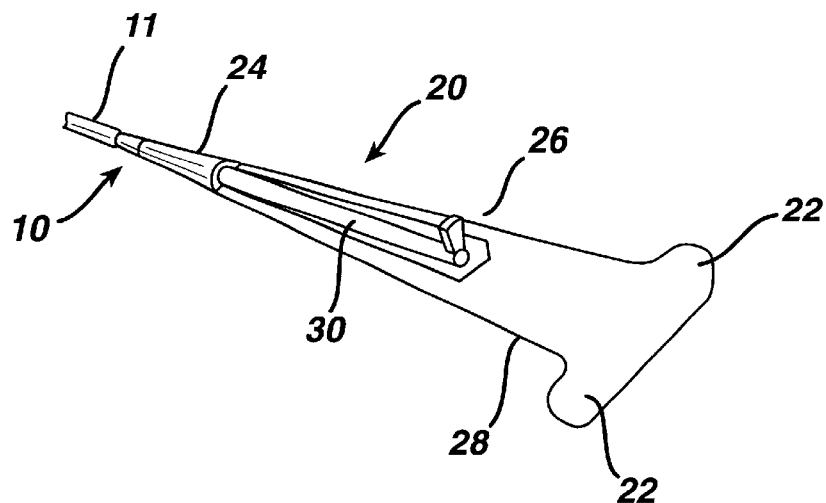
FIG. 5 is a perspective view of the lower casing part of the handle with the locking means inserted.
Figure 6:
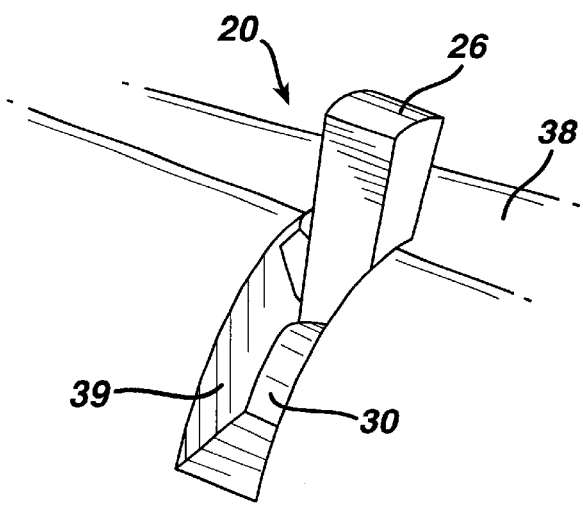
FIG. 6 is a detailed view of the locking handle.

The actuating lever 26 extends from the proximal end region of the sleeve 30 and runs generally in radial direction. FIG. 5 shows the lower casing part 28 of the handle with the sleeve 30 inserted. In the detailed view of FIG. 6, the upper casing 38 is shown. It can be recognized that the free end of the actuating lever 26 projects through an opening 39 in the upper casing 38. The opening 39 allows a rotating movement of the actuating lever 26 by about 90° such that, by adjusting the actuating lever 26, the sleeve 30 can be rotated from the locking position to the release position. In FIG. 6, the actuating lever 26 is in the locking position, wherein an engagement protrusion 36 (see FIG. 4) is located in a corresponding depression at the upper casing part 38 such that the actuating lever 26 is secured against an unintentional movement. This lock can be overcome when a larger force is applied such that the actuating lever 26 can be rotated to the release position.

Figure 7:
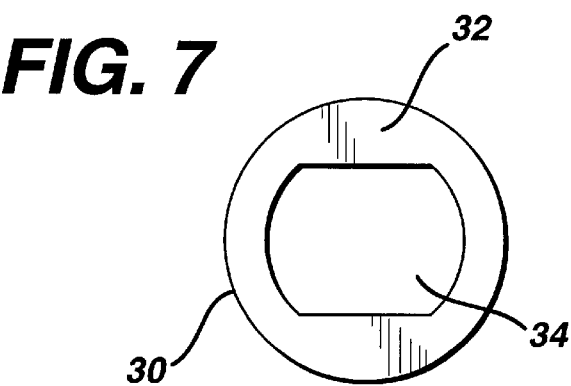
FIG. 7 is an elevation view of the distal end face of the sleeve of the locking means.

FIG. 7 displays the distal end of the sleeve 30 with the locking element 32 and the opening 34.

Figure 8:
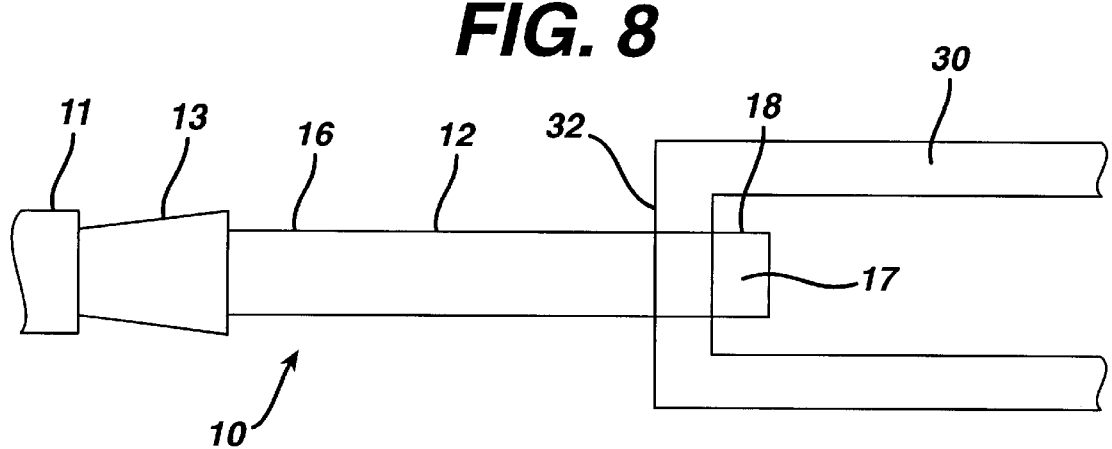
FIG. 8 is a schematic longitudinal sectional elevation view illustrating the release position of the locking means, the plane of the paper being given by the direction of the axis I from FIG. 3.
Figure 9:
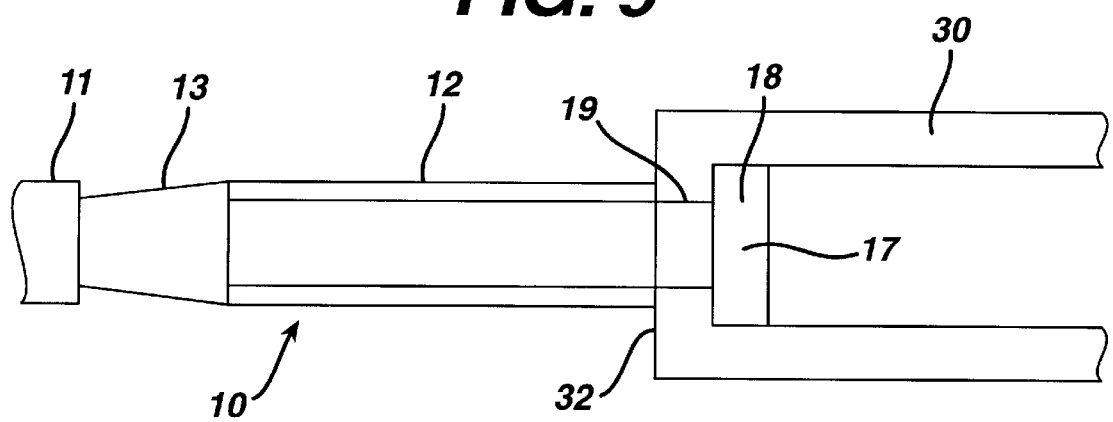
FIG. 9 is a schematic longitudinal sectional elevation view illustrating the locking position of the locking means, the plane of the paper being given by the direction of the axis II from FIG. 3.

In FIGS. 8 and 9, the mode of operation of the locking means is illustrated. In the state shown in FIG. 8, the sleeve 30 is in the release position, wherein the locking element 32 is aligned with respect to the opening 34 and thus fits therethrough. The locking position is shown in FIG. 9. It can be recognized that the depression 19 is located in the area of the locking element 32 and that the locking protrusion 17 prevents the needle 10 from being pulled out. The locking position is achieved by rotating the sleeve 30 by about 90°. It has to be noticed that in the sectional representation according to FIG. 9 the plane of the paper has been rotated by 90' as well (see also FIG. 3) such that seemingly the needle 10 has been rotated and not the sleeve 30.

Figure 10:
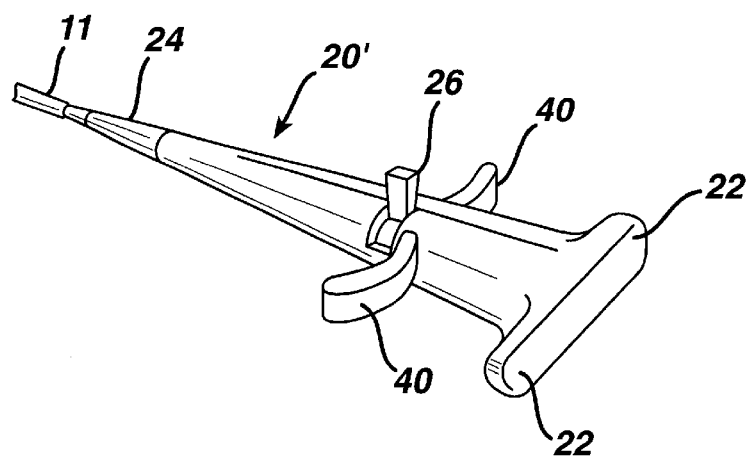
FIG. 10 a perspective view of the handle of a second embodiment of the system according to the invention.

FIG. 10 shows a variant of the handle, which is designated by 20'. In addition to both broadening structures 22, the handle 20, has two finger application structures 40 which enable an even more convenient handling. The surgeon can grasp the handle 20' such that the broadening structures 22 are positioned in his palm whereas his index finger and his middle finger grip around the finger application structures 40 and thus slightly press the handle 20 against the palm. Therefore, the handle 20 rests more economically and safely in, the hand of the surgeon. The actuating lever 26 can be rotated with the thumb of the same hand. Thus, a convenient actuation with one hand is possible.

As explained above, the handle 20 appreciably facilitates the guidance and use of the surgical needle 10 inserted into the handle 20. When the actuating lever 26 is in the locking position, the handle 20 and the needle 10 are firmly connected to each other. If, however, the handle 20 obstructs the further application of the needle 10 and the needle 10 has to be released, the actuating lever 26 can be easily rotated into the release position such that the needle 10 and the handle 20 can be separated by a relative motion in longitudinal direction without problems and jerks.

Figure 11D:
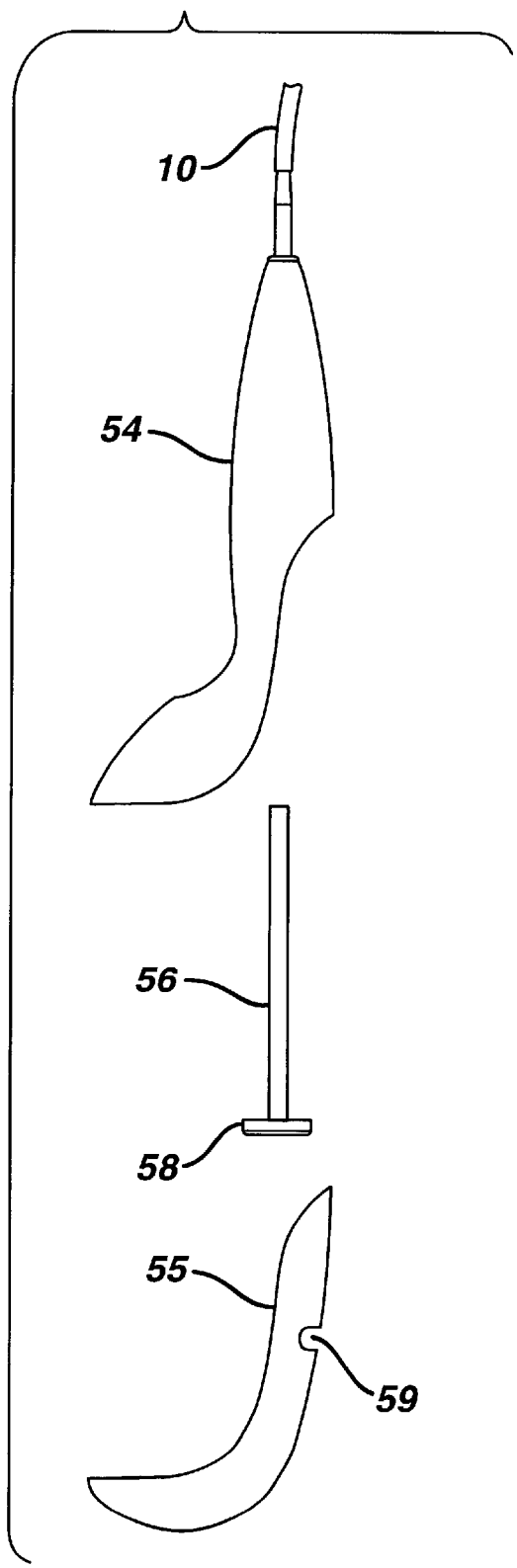

FIG. 11 shows several views of a third embodiment of the system according to the invention, i.e. (a) from the top, (b) from the front, (c) from the side, and (d) in a schematic explosion view. The needle, again designated by 10, is similarly designed as before, whereas the handle, designated by 50, has a particular ergonomic shape with one lateral broadening structure 52 only. The handle 50 comprises two casing parts 54 and 55 inside which a sleeve 56 is mounted in a rotatable manner which is designed similar as in the first two embodiments. An actuating lever 58 is accessible through an opening 59 in the casing part 55 in order to rotate the sleeve 56 from the locking position into the release position.

FIG. 12 displays several views of a fourth embodiment of the system according to the invention, i.e. (a) from the top, (b) from the side, (c) from the front, and (d) from below. Again, the needle is designated by 10. The handle, provided with the reference numeral 60, comprises a gripping bow 62 as a broadening structure. The casing is in two-part form again with casing parts 64 and 65. A lever 66 serves as an actuating lever of a rotatable sleeve, which is similarly designed as in the previous embodiments and is not shown in FIG. 12. The lever 66 is arranged at the end of the sleeve.

It will be apparent from the foregoing that, while particular forms of the invention have been illustrated and described, various modifications can be made without departing from the spirit and scope of the invention. Accordingly, it is not intended that the invention be limited, except as by the appended claims.

What is claimed is:

1. A handle for accepting a surgical needle for use in surgical procedures, the surgical needle having a proximal end region including a locking protrusion at a first end thereof, wherein said locking protrusion and at least a portion or said proximal end region have a non-circular cross-section, the handle comprising:
   a lumen having a non-circular cross-section substantially similar to that of the surgical needle portion, and dimensioned to receive therein the surgical needle portion and locking protrusion;
   a locking device non-threadably movable between a first position wherein, when the surgical needle portion is received within the lumen, the locking device non-threadably engages the locking protrusion to lock the surgical needle within the lumen and a second position allowing the surgical needle to be placed within or removed from the lumen; and
   an upper casing having a channel therein adapted to receive the surgical needle locking protrusion, and an opening therethrough,
   wherein the locking device further comprises a sleeve and an actuating device extending outwardly therefrom, wherein the sleeve is positioned within the casing and the actuating device extends outwardly through the upper casing opening.

2. A handle according to claim 1, wherein when the surgical needle locking protrusion is received within the upper casing channel, and when the locking device is in the first position, the locking device engages the locking protrusion to thereby prevent the needle from being removed from the lumen.

3. The handle according to claim 2, wherein a distal end of the locking device includes a locking element having an opening therein having a shape substantially corresponding to the cross-section of the locking protrusion, wherein when the locking protrusion is received within the channel, when the locking device is in the first position the locking element opening is substantially aligned with the locking protrusion, and when in the second position the locking element opening is not aligned with the locking protrusion.

4. A handle and surgical needle combination comprising:
   a surgical needle having a proximal end region including a support section, a depression portion positioned proximal of the support section, and a locking protrusion positioned proximal of the depression portion, wherein the support section and locking protrusion have substantially similar, non-circular cross-sections, and wherein the depression has a cross-section less than that of the support section and locking protrusion;
   a handle having a distal end and a first lumen therein extending in a proximal direction from an opening at the distal end, the first lumen having a cross-section substantially corresponding to the cross-section of the support section and locking protrusion and adapted to receive therein the support section and locking protrusion, and having a length such that, when received therein, the depression and locking protrusion are external to the lumen,
   the handle further comprising a locking device including a sleeve having a channel therein and having at a distal end a locking element including an opening having a shape substantially corresponding to the cross-section of the locking protrusion and adapted to receive therethrough the locking protrusion, wherein the sleeve is movable between a first position wherein the locking element opening is substantially aligned with first lumen so that the locking protrusion may be inserted into or removed from within the channel, and a second position wherein the locking element opening is not aligned with the first lumen so that, when the locking protrusion is inserted within the channel, the locking element engages the locking protrusion to thereby prevent removal from within the channel.

5. The combination of claim 4, wherein the proximal end region of the surgical needle further comprises a depression, which engages, in the first position, the locking element.

6. The combination of claim 4, wherein the proximal end region of the needle comprises an attachment means for attaching a suture material or mesh tape to the needle.

7. A handle and surgical needle combination comprising:
   a surgical needle having a proximal end region including a first portion and a locking protrusion both having a non-circular cross-section; and
   a handle having a first lumen therein extending in a proximal direction from an opening at a distal end of the handle, the lumen having a cross-section substantially similar to the cross-section of the needle first portion, and adapted to receive therein the needle first portion and locking protrusion, and a locking device non-threadably movable between a first position wherein it non-threadably engages the locking protrusion to thereby prevent removal of the needle from the handle, and a second position allowing the needle to be inserted into and removed from the handle, wherein the locking device includes a sleeve having a channel therein and having at a distal end a locking element including an opening sized and shaped to substantially correspond to the cross-section of the locking protrusion and adapted to receive therethrough the locking protrusion.

8. The combination according to claim 7, wherein the proximal end region of the needle further comprises a depression positioned adjacent to and distal of the locking protrusion, the depression having a cross-section smaller than that of the locking protrusion.

9. The combination according to claim 8, wherein when the locking protrusion is received through the locking element opening, the locking element is positioned adjacent to the depression.

10. The combination according to claim 9, wherein movement of the locking device from the second to the first position moves the locking element opening from a first position in which it is substantially aligned with the locking protrusion, to a second position in which it is not substantially aligned with the locking protrusion, thereby preventing the locking protrusion from passing therethrough.

11. A method for treating female urinary incontinence in a female patient comprising the steps of:
   a) providing a first and second curved needle element each defining in part a curved shaft having a proximal end region including a first portion having a non-circular cross-section and a locking protrusion positioned at a first end; and a tape for attaching to the first and second needles;
   b) providing a handle having a distal end and a lumen therein extending in a proximal direction from an opening at the distal end, the lumen having a cross-section substantially similar to the cross-section of the first portion of the needle and adapted to receive therein the needle first portion and locking protrusion, the handle further having a locking device non-threadably movable between a first position wherein the locking device non-threadably engages the locking protrusion to thereby prevent removal of the surgical needle from the handle, and a second position allowing the needle to be inserted into and removed from the handle;
   c) attaching a first end of the tape to the first needle;
   d) inserting the first portion of the first needle into the handle lumen and moving the locking device to the first position;
   e) passing the first needle and tape into a patient's body on one side of the patient's urethra;
   f) moving the locking device to the second position and removing the first needle from the handle;
   g) inserting the first portion of the second needle into the handle lumen and moving the locking device to the first position;
   h) passing the second needle and tape into the body on the opposite side of the urethra;
   i) moving the locking device to the second position and removing the second needle from the handle; and
   k) adjusting the tape to form a supporting sling around the urethra.

12. The method of claim 11 wherein the needle is passed into the body in steps (e) and (h) via the patient's vagina.

13. The method of claim 11 wherein the needle is passed into the body in steps (e) and (h) via the patient's abdomen.

* * * * *